(12) United States Patent
Butterfield et al.

(10) Patent No.: US 6,616,633 B1
(45) Date of Patent: *Sep. 9, 2003

(54) APPARATUS AND METHOD FOR AIR-IN-LINE DETECTION

(75) Inventors: Robert D. Butterfield, Poway, CA (US); Allen B. Farquhar, San Diego, CA (US)

(73) Assignee: Alaris Medical Systems, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/933,709

(22) Filed: Sep. 19, 1997

(51) Int. Cl.[7] .............................................. A61M 1/00
(52) U.S. Cl. ........................................ 604/151; 604/67
(58) Field of Search ..................... 604/65–67, 122–125, 604/93, 131, 151, 118, 246; 73/19.01, 602; 128/DIG. 13; 600/345–348, 431, 432; 702/45, 23, 194

(56) References Cited

U.S. PATENT DOCUMENTS

| 3,819,919 | A | * | 6/1974 | McGunigle ............ 235/151.34 |
| 3,974,681 | A | | 8/1976 | Namery |
| 4,068,521 | A | | 1/1978 | Cosentino et al. |
| 4,114,144 | A | | 9/1978 | Hyman |
| 4,217,993 | A | | 8/1980 | Jess et al. |
| 4,312,341 | A | | 1/1982 | Zissimopoulos et al. |
| 4,321,461 | A | | 3/1982 | Walter, Jr. et al. |
| 4,344,429 | A | | 8/1982 | Gupton et al. |
| 4,366,384 | A | | 12/1982 | Jensen |
| 4,367,736 | A | | 1/1983 | Gupton |
| 4,418,565 | A | | 12/1983 | St. John |
| 4,559,454 | A | | 12/1985 | Kramer |
| 4,607,520 | A | | 8/1986 | Dam |
| 4,658,244 | A | | 4/1987 | Meijer |
| 4,673,927 | A | | 6/1987 | Cianciavicchia |
| 4,722,224 | A | | 2/1988 | Scheller et al. |
| 4,762,518 | A | | 8/1988 | Kreinick |
| 4,764,166 | A | | 8/1988 | Sapni |
| 4,784,643 | A | | 11/1988 | Siretchi et al. |
| 4,821,558 | A | | 4/1989 | Pastrone et al. |
| 4,829,448 | A | | 5/1989 | Balding et al. |
| 4,857,050 | A | | 8/1989 | Lentz et al. |
| 4,881,413 | A | | 11/1989 | Georgi et al. |
| 4,959,050 | A | | 9/1990 | Bobo, Jr. |
| 5,006,110 | A | | 4/1991 | Garrison et al. |
| 5,041,086 | A | | 8/1991 | Koenig et al. |
| 5,059,171 | A | | 10/1991 | Bridge et al. |
| 5,064,412 | A | * | 11/1991 | Henke et al. .................. 604/65 |
| 5,102,392 | A | | 4/1992 | Sakai et al. |
| 5,103,211 | A | | 4/1992 | Daoud et al. |
| 5,123,275 | A | | 6/1992 | Daoud et al. |
| 5,176,631 | A | * | 1/1993 | Koenig ......................... 604/65 |

(List continued on next page.)

Primary Examiner—Glenn K. Dawson
Assistant Examiner—Jennifer Maynard
(74) Attorney, Agent, or Firm—Fulwider Patton Lee & Utecht, LLP

(57) ABSTRACT

The concentration of air or other agents in a fluid delivery line is determined by monitoring agent signals and processing those agent signals along with information regarding the age of each agent signal. The processor determines a primary agent concentration value based on the received agent signal values, with the primary agent concentration value determined by giving greater weight to more recent agent signal values. Where the primary agent concentration value exceeds a primary threshold value, an alarm signal may be activated. The processor also may determine a secondary agent concentration value, which may be determined from the actual agent signal values instead of the weighted agent signal values. Where the secondary agent concentration value exceeds a secondary threshold value, an alarm signal may be activated.

28 Claims, 9 Drawing Sheets

U.S. PATENT DOCUMENTS

| | | |
|---|---|---|
| 5,177,993 A | 1/1993 | Beckman et al. |
| 5,180,287 A * | 1/1993 | Natwick et al. ............... 417/43 |
| 5,211,201 A | 5/1993 | Kamen et al. |
| 5,260,665 A * | 11/1993 | Goldberg et al. ........... 324/636 |
| 5,394,732 A | 3/1995 | Johnson et al. |
| 5,455,423 A * | 10/1995 | Mount et al. ................ 250/343 |
| 5,483,222 A * | 1/1996 | Tice ........................... 340/518 |
| 5,537,853 A * | 7/1996 | Finburgh et al. ........... 73/19.03 |
| 5,616,124 A | 4/1997 | Hauge et al. |
| 5,704,311 A * | 1/1998 | van den Berg .......... 119/14.02 |
| 5,715,796 A * | 2/1998 | Suzuki et al. ................ 123/492 |
| 5,865,174 A * | 2/1999 | Kloeppel ............... 128/204.23 |
| 5,965,089 A * | 10/1999 | Jarvik et al. ................... 422/44 |
| 6,142,008 A * | 11/2000 | Cole et al. .................. 73/19.03 |
| 6,411,833 B1 * | 6/2002 | Baker, Jr. et al. ........... 600/336 |

* cited by examiner

APPARATUS AND METHOD FOR AIR-IN-LINE DETECTION

BACKGROUND OF THE INVENTION

1. Field of the Invention

The invention relates to fluid delivery systems. More particularly, the present invention relates to detecting air and other agents in a fluid delivery system infusing fluid to a patient.

2. Description of Related Art

There are a variety of situations where fluid is infused to a patient. Applications of fluid delivery systems include (but are by no means limited to) intravenous infusion, intra-arterial infusion, infusion of enteral solutions, infusion of medication to the epidural space, and diagnostic infusion to determine vascular characteristics of the arterial, urinary, lymphatic, or cerebrospinal systems.

Fluid delivery systems for infusing fluid to a patient typically include a supply of the fluid to be administered, an infusion needle or cannula, an administration set connecting the fluid supply to the cannula, and a flow control device, such as a positive displacement infusion pump. The administration set typically comprises a length of flexible tubing. The cannula is mounted at the distal end of the flexible tubing for insertion into a patient's blood vessel or other body location to deliver the fluid infusate to the patient.

During an infusion procedure, various agents, the most typical of which is air, can be introduced into the fluid delivery system by a number of events, including the fluid supply becoming drained of fluid. Because introducing excessive air into the patient's blood system may create complications, it is desirable to detect the introduction of air into the fluid delivery system before substantial amounts of air are introduced into the patient. When substantial amounts of air are detected in the fluid delivery system, fluid delivery can be terminated until a health care provider can correct the underlying problem, such as by refilling or replacing the fluid supply.

Sometimes, a temporary event, such as the accumulation of small quantities of air from outgassing of air suspended in the solution, may cause a very few small air bubbles to enter the system. Where the amount of air is quite small, the patient may be able to safely absorb the small air amounts, so that stopping operation of the pump is unnecessary. Thus, it is desirable to not only detect the air in the fluid delivery system, but also to evaluate the amount of air present.

One technique for determining the amount of air in a fluid delivery system, such as a length of intravenous tubing, is through the use of sensors such as light or ultrasonic sensors. In such a technique, electromagnetic energy, such as light, or sound energy, such as an ultrasonic pulse, is passed through the intravenous tubing, and the sensor monitors variations in the received energy. Because air generally transmits light and/or sound energy in a different fashion than do intravenous fluid solutions, due to different transmission properties such as absorption and/or refractivity, monitoring variations in the light's or sound's ability to pass through the solution can give a generally accurate determination that air exists in the fluid line.

A more difficult problem is determining just how much air is in the fluid line, and how much will be delivered to the patient. For example, at a particular point in time, a sensor looking at just a very short section of the tubing may see only air in the line, with no intravenous fluid solution present. This may be the result of the fluid supply being entirely empty, in which case the fluid delivery system should be shut down. However, a single small air bubble may also cause the same sensor reading, and shutting down the fluid delivery system on account of a single air bubble may be inappropriate.

A small amount of air may be of no consequence where no significant amounts of air are in the delivery system either upstream or downstream of the sensor section. Where the small amount of air is part of a continuous stream of small air bubbles in the tubing, however, the sum of the small bubbles may amount to a significant amount of air, so that the fluid supply system should be shut off pending correction of the underlying problem.

A method of accounting for the limitations of monitoring just a short section of the tubing is to install several sensors along the length of the tubing, thereby monitoring a much longer section of tubing. The addition of multiple sensors and their associated electronics can, however, substantially add to the cost and complexity of the fluid delivery system. Moreover, such use of multiple sensors may still not accurately determine the amount of air in the line over long periods of time or as large volumes of fluid pass therethrough.

A further method is to keep a running total of the air that passes through the tubing section. When the total air reaches a certain threshold, the fluid delivery system can be shut down to await correction of the underlying problem by appropriate personnel. Such a simple running total may not, however, adequately reflect the actual ability of the patient's system to safely absorb air.

Hence, those skilled in the art have recognized a need for a fluid delivery monitoring system that can detect air in the fluid, but that can also take into account the total air over a period of time or in a volume of fluid, as well as to account for other factors, such as the ability of the patient's body to safely absorb some air during fluid volume infusion. The present invention satisfies these needs and others.

SUMMARY OF THE INVENTION

Briefly and in general terms, the present invention is directed to an apparatus and method for monitoring concentrations of air or other agents, such as undesirable impurities, mixed into a fluid supply system. The invention has particular application in detecting air in a fluid supply system.

The invention includes an agent sensor coupled to a fluid conduit for providing signals in response to agents sensed in the fluid conduit. A processor receives the agent signals from the agent sensor, determining one or more weighted agent signal values by applying a weighting value to one or more of the agent signals based on the volume delivered since each agent signal was received, and determines an agent concentration value from the weighted agent signal values. The processor may compare the agent concentration value to an alarm threshold and, in response to the agent concentration value exceeding the alarm threshold, provide an alarm signal that activates an alarm.

The apparatus may further include a fluid control device, such as a peristaltic pump, acting on a section of the fluid conduit to control the flow of fluid through the fluid conduit, with the processor controlling the fluid control device. In response to the agent concentration value exceeding the alarm threshold, the processor may cause the fluid control device to stop fluid from flowing through the fluid conduit.

The agent sensor may comprise almost any type of sensor capable of detecting agents in a fluid, such as an ultrasonic air detector or an air detector that uses electromagnetic energy, such as light, to detect air in the system. In a preferred embodiment, the agent sensor is an air sensor.

The apparatus may be part of an overall fluid delivery system for introducing fluid to a patient, including a fluid source, a fluid conduit downstream of and in fluid communication with the fluid source, a cannula in fluid communication with the fluid source and configured to be introduced into a patient's body to provide fluid thereto, an agent sensor coupled to the fluid conduit for providing signals in response to agent sensed in the fluid conduit, and a processor that receives the agent signals from the agent sensor, determines a weighted agent signal value of each agent signal based on the signal and the volume delivered since the signal was received, and processes several weighted agent signal values to determine a primary agent concentration value. The primary agent concentration value is compared to an alarm threshold, and an alarm is activated if the threshold is exceeded.

The agent concentration value may be determined by applying a weighting value to each agent signal as a separate calculation. The weighting value applied to each agent signal value may change based upon the "age" of an agent signal. For example, the weighting value may decrease for "older" (i.e., less recently received) agent signal values. The "age" of an agent signal may be defined as the volume of fluid that has passed since that particular agent signal value was received and/or generated. The "age" may also be determined as the actual time that has elapsed since receipt and/or generation of the agent signal value.

The weighting value may take into account numerous parameters. For example, the weighting value may itself be a function of the volume of fluid moved in each sample and the size of the volume window.

The agent concentration value may also be determined by applying a weighting factor to a past agent concentration value, thereby applying that weighting factor to older agent signal values. In such an embodiment, the older agent signal values will effectively have the weighting factor applied to them more often than more recent signal values. If the weighting factor is less than 1, these repeated applications of the weighting factor will cause older signal values to have decreased impact on the agent concentration value.

The invention may further include providing, over a period of time and/or during infusion of a volume of fluid, a second series of agent signal values, and determining a secondary agent concentration value. In one embodiment, the secondary agent concentration value may include weighting values, which may be the same or different from the weighting values used to determine the primary agent concentration value. Alternatively, the secondary agent concentration value may use no weighting values. The secondary agent concentration value can be compared to a secondary threshold, which may be a single bubble threshold, and an alarm may be activated in response to the secondary threshold being exceeded by the secondary agent concentration value.

Other features and advantages of the present invention will become more apparent from the following detailed description of the invention when taken in conjunction with the accompanying drawings.

DETAILED DESCRIPTION OF THE PREFERRED EMBODIMENTS

Figure 1:
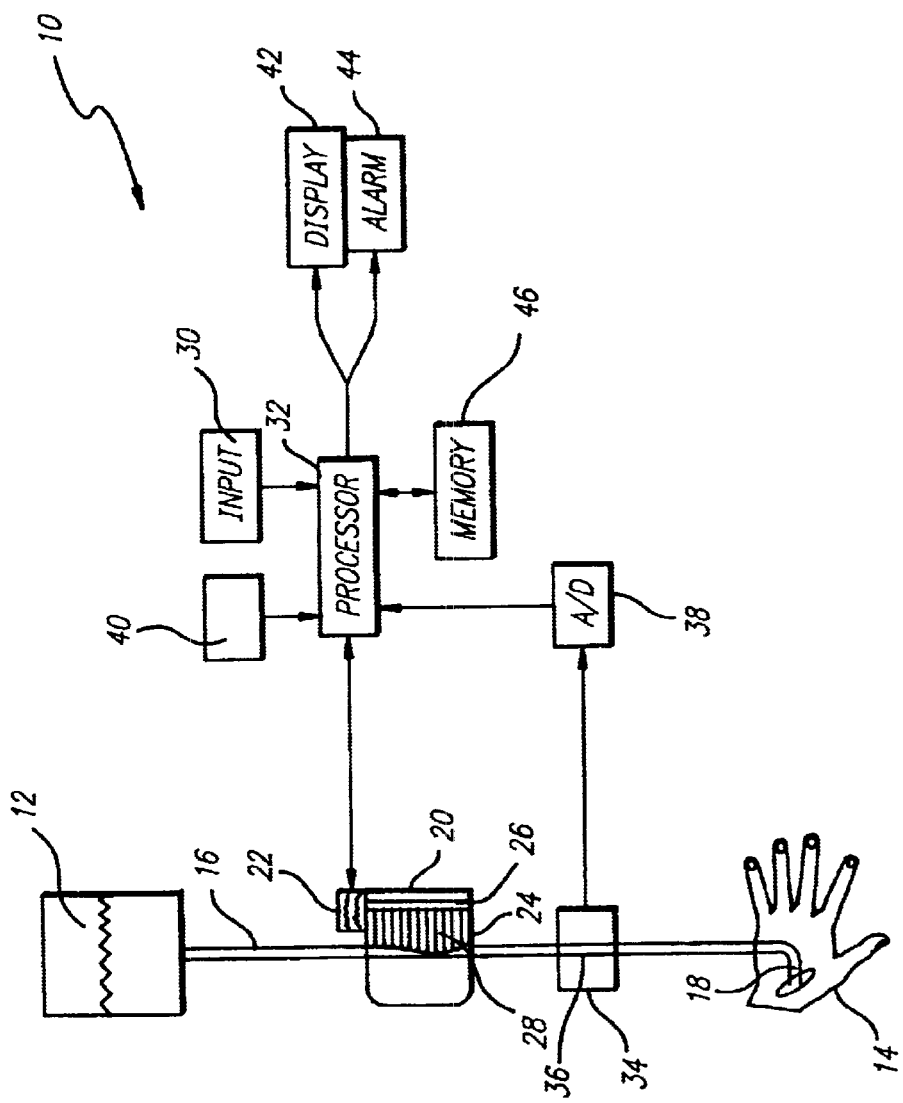
FIG. 1 is a simplified block diagram of a system for detecting agents in a fluid line incorporating the principles of the invention as applied to an intravascular fluid infusion system.

Referring now to the drawings with more particularity, wherein like reference numerals in the separate views indicate like or corresponding elements, there is shown in FIG. 1 a block diagram of a fluid delivery system 10 incorporating aspects of the current invention. The fluid delivery system includes a fluid source 12 supplying fluid to a patient 14 via a fluid conduit 16 and cannula 18. In the embodiment of FIG. 1, a flow control device 20 controls the flow of fluid through the conduit. The flow control device may include a pump motor 22 driving a pumping mechanism 24, which in the embodiment shown comprises a rotating cam shaft 26 coupled to the pump motor 22 and moving a series of peristaltic elements 28. The peristaltic elements 28 operate on the conduit 16 to move fluid from the fluid source 12, through the conduit 16, and into the patient 14 via the cannula 18.

In the embodiment of FIG. 1, a user input device 30, such as a keypad, provides operator instructions, such as flow rate selection, to a processor 32. The processor 32 controls the operation of the pump motor 22 driving the pumping mechanism 24. A motor position sensor (not shown) determines the position of the pump motor 22 and pumping mechanism 24, and provides a position signal to the processor 32.

Located along a section 36 of the fluid conduit is a sensor 34 coupled to the conduit 16 to sense agents in that particular fluid conduit section 36. In the embodiment depicted, the sensor 34 is an air sensor that detects air in the conduit section 36. An analog-to-digital converter 38 ("A-to-D") receives the output signals from the sensor 34 and converts them to a digital format at a particular sample rate controlled by the processor 32. The output signals indicate the amount of air in the line at a particular point in time. An age determiner, such as a volume accumulator 40, provides an age value for the output digital signals, with the age value a function of the volume that has been introduced through the fluid line. (A clock could also provide an age value based upon the time that the output digital signal is generated or received, depending on the particular system.) The processor 32 receives the digital signals, processes them as described in more detail below, and determines an air concentration value representing air passing through the fluid delivery system 10. A display 42 may present an indication of the air concentration value. One or more alarms 44 are provided to indicate an unsatisfactory air concentration value.

The air signals may be stored in a memory 46, which may also provide various threshold values to the processor 32. In one embodiment, the processor 32 applies a weighting value to each air signal, with the weighting value a function of the age of the output air signal. Note that age may be determined based on elapsed time or based on the volume of fluid that has passed since the event occurred. For example, the age of an output air signal may be determined as the volume of fluid that has entered the fluid line since the particular air signal was received.

Figure 2:
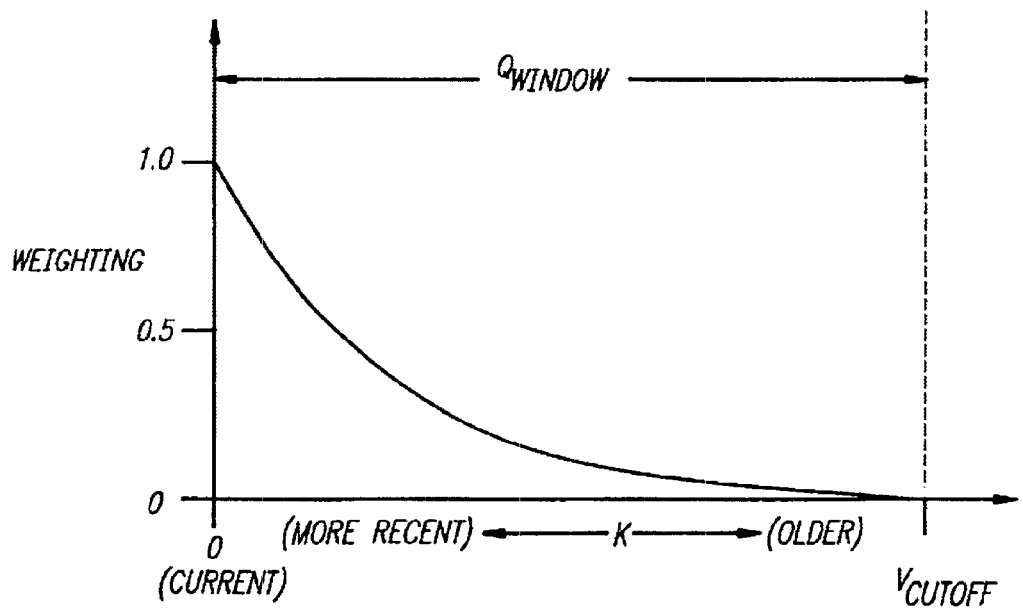
FIG. 2 is a graph depicting weighting values as a function of the age of various air signals.

As shown in FIG. 2, where K represents the age of the air signals, in one embodiment the weighting value is largest for the most recent output air signals, and drops off for older output air signals. (Note that the weighting values shown in FIGS. 2 and 3, including the maximum value of 1.0, are for illustrative purposes only.) In the embodiment depicted in FIG. 2, air signals that are older than a cutoff age $V_{cutoff}$ are discarded, as may occur where a limited number of memory registers are exceeded and older values are displaced by younger values. In the embodiment shown, the age of the air signal is determined as the volume pumped into the IV system, so that the volume window Qwindow is the volume of fluid pumped into the IV system in the period between the present time 0 and the cutoff age $V_{cutoff}$.

Figure 3:
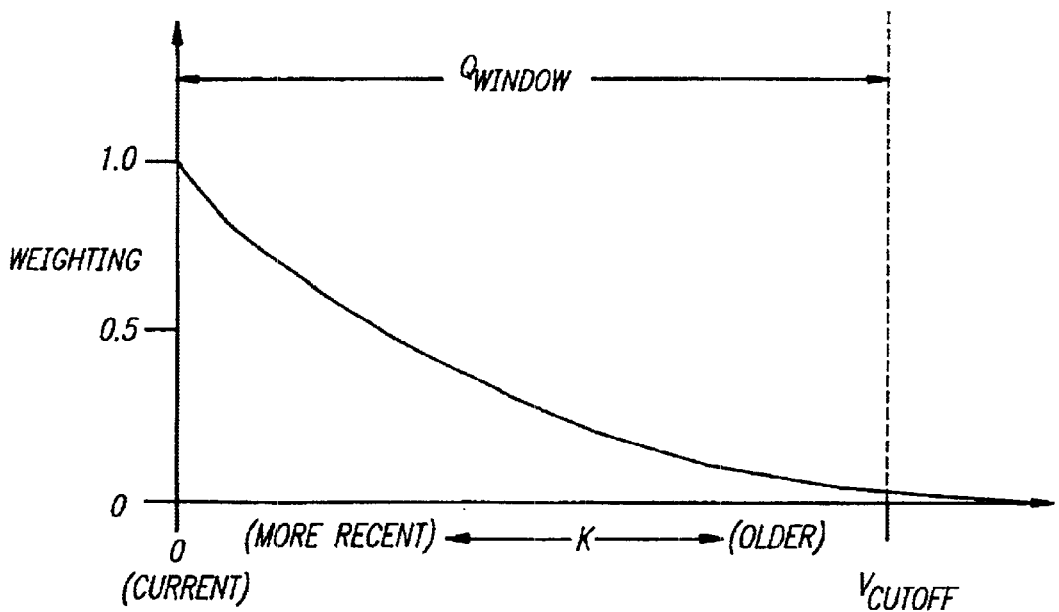
FIG. 3 is a graph depicting weighting values as a function of the age of various air signals.

FIG. 3 shows another embodiment, but wherein there is no cutoff age $V_{cutoff}$. Instead, the older output air signals are given weightings that approach, but do not actually reach, zero. Note that even though older output air signals are not discarded, their weightings eventually become so small as to be negligible, so that a volume window Qwindow can be an effective representation of the volume of fluid pumped during the period in which air signals are given a significant weighting.

In such embodiments, the air concentration value can be determined via a formula such as the following:

$$AirConcentration(0) = \sum_{K=0}^{N-1} (AirSignal(K) \times b \times a^K) \quad (1)$$

where AirSignal(0) is the current (i.e., most recent) air signal, AirSignal(1) is the next to the most recent air signal, etc.; N is the total number of air signals used to determine the air concentration value; and b and a are weighting factors. If the weighting factor a is less than zero, then "older" airsignal values, such as where K>>0, will be given progressively less weight due to the shrinking of the value $a^k$ in the above formula. The above equation is only one example of such a formula —numerous other formulae are also well within the scope of the invention, so long as the effect is to give differing weights to different air signal values. In the embodiment depicted in Equation 1, the weighting factor a ("PastWeight") is used to vary the air signal weightings according to the age of the air signal value, represented by the value K, while the application of weighting factor b ("CurrentWeight") is unaffected by the age of the air signal value.

The weighting factors may be variables that take into account operational characteristics of the system, such as fluid flow rate, desired sensitivity, etc, which may vary during pump operation. For example, a weighting factor may be a function of various parameters, such as the volume of fluid (Qsample) pumped over the period to which the air signal value corresponds (which may vary depending on pump flow rate and the particular pump steps and/or groups of steps), and the desired volume of fluid (Qwindow) over which the air signal values are given relevant weightings. In one embodiment, the weighting factor a (PastWeight) is a function of Qwindow and Qsample, as follows:

$$AirConcentration(0) = \sum_{K=0}^{N-1} \left( AirSignal(K) \times b \times e^{\frac{-K \times Qsample}{Qwindow/3}} \right) \quad (2)$$

Figure 5A:
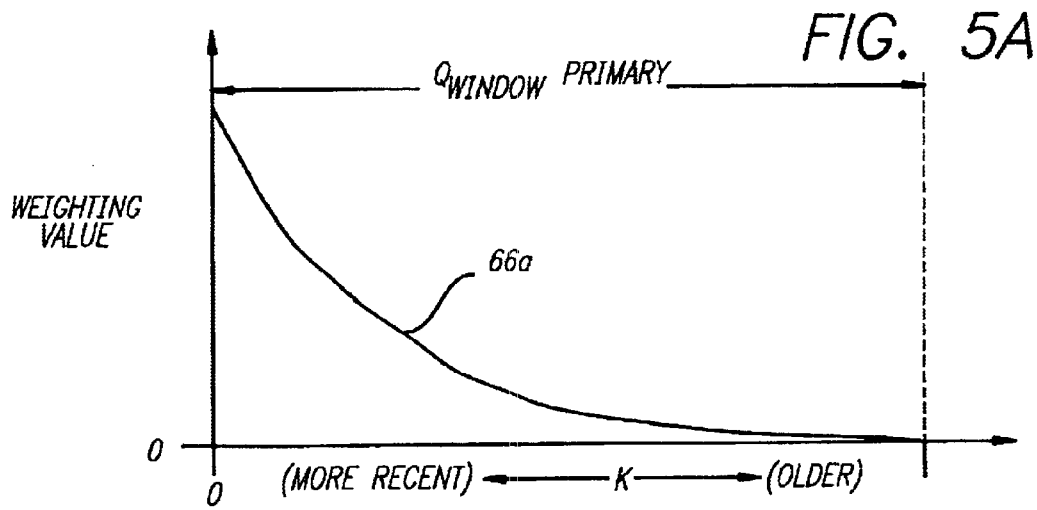
FIG. 5a is a graph depicting a varying weighting value as a function of the age of various air signals.
Figure 5B:
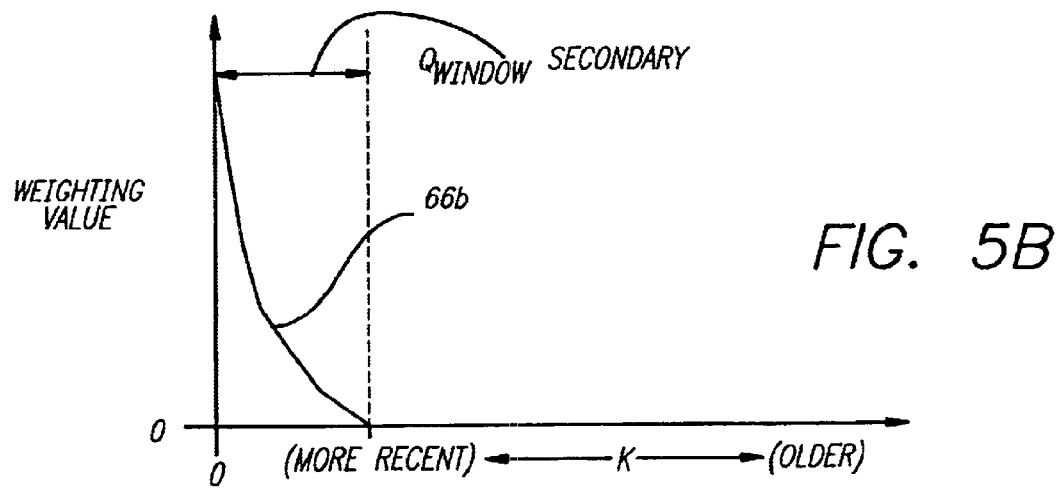
FIG. 5b is a graph depicting a varying weighting value as a function of the age of various air signals.

Thus the FIG. 5b current air sample, AirSignal(0), is given a weighting of b (because $e^0=1$). The next most recent air sample, AirSignal(1), is weighted by $$e^{\frac{-Qsample}{Qwindow/3}} \quad (3)$$

and so on.

Note that Equation 2 is merely one simplified example of such a formula. Other formulae are also within the scope of the invention. For example, the weighting factor b may be a function of Qwindow and Qsample and/or of weighting factor a. For example, with a defined as set forth in Equation 2, the value b could be defined by the formula b=1−a.

In Equation 2, K goes from 0 to N−1, indicating that a number N of air signals are used to determine the air concentration value. N may be a very large or infinite number, as was depicted in FIG. 3. However, in some circumstances, such as where only a limited number of memory registers are available to store individual air signal values, the number N may be much smaller. In practicality, the number of air signal values received over an extended period may grow to be quite large, which may require discarding of older air signal values, as depicted in FIG. 2.

One option for dealing with the large number of air signal values received over a long period is to store them in a memory 46, depicted in FIG. 1, that may include "volume delivered" or time references indicating the age of the output air signal values. Newer air signal values may be stored, with older values shifted downward on the register. The oldest air signal values may be discarded as the registers are filled, thus making way for newer values.

Figure 4:
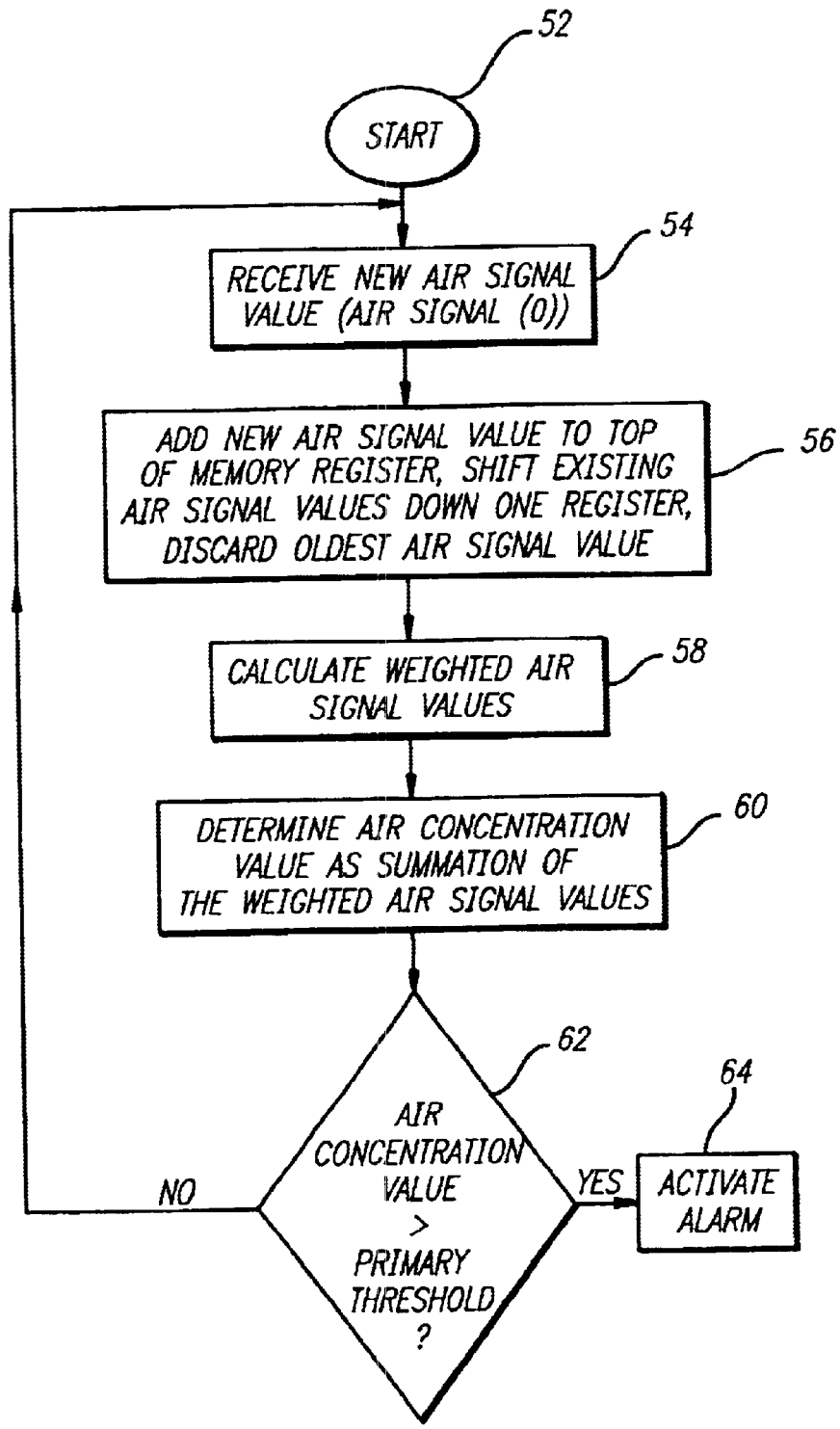
FIG. 4 is a simplified flowchart showing a process for determining air concentration in a fluid line according to one embodiment of the invention.

FIG. 4 is a simplified flowchart depicting a process for determining air concentration in a fluid line according to one embodiment of the invention. After system start 52 (or a reset, such as a user-initiated manual reset), step 54 includes receiving a new air signal value, which is added to the top of the memory register at step 56. Step 56 includes shifting existing air signal values down in the memory register, with the oldest air signal value being discarded. At step 58, the air signals are weighted according to their age, to generate weighted air signal values. At step 60, the processor adds the weighted air signal values together to determine an air concentration value. At step 62, the air concentration value is compared to a primary threshold value, also known as an air density threshold. Where the air concentration value exceeds the primary threshold, an alarm is sounded (step 64). The system may also operate to stop further delivery of fluid through the conduit when the air density threshold is exceeded. If the threshold is not exceeded, the system prepares to repeat the cycle. The system then returns to step 54 and receives a new air signal value.

In one embodiment, the system continuously updates the calculated air concentration value. For example, in the embodiment depicted in FIG. 4, each time a new air signal value is received by the processor, the system determines a new air concentration value and compares it to a primary threshold value. If the new air concentration value exceeds the primary threshold value, an alarm is sounded.

The primary threshold value may be set through a variety of techniques. The primary threshold value may be a single fixed value that is preprogrammed into the system. The primary threshold value may also be selected by a user. The primary threshold value may vary as a function of one or more parameters such as the particular fluid, patient characteristics (such as weight), or the flow rate through the fluid conduit. The primary threshold may be determined from a formula with one or more variables, or may be selected from a table of several primary threshold values.

Comparing the air concentration value to the primary threshold value is helpful in rapidly detecting excessive air in the fluid conduit while preventing false alarms. However, the primary threshold and air concentration value comparison may not be the most desirable method for detecting all fluid flow anomalies. For example, where a fluid delivery system has had almost no air and suddenly runs out of fluid, a large air pocket will typically be introduced into the system. In such a situation, comparing the air concentration value to primary threshold value will typically cause the alarm to sound prior to a significant amount of air being introduced to the patient, but significant amounts of air may be introduced into the IV system itself (but well upstream of the patient) prior to alarm activation. To minimize the amount of air introduced into the IV system and reduce system downtime, it would be desirable if the alarm were sounded as rapidly as possible so that an attendant can rapidly refill or replace the fluid supply.

To increase the system's ability to rapidly sound an alarm in various situations, the system may include a secondary threshold value to which is compared a secondary air concentration value. The secondary air concentration value may be an air concentration value which is determined in parallel or in tandem with the primary averaged concentration value. The secondary air concentration value may be determined with a weighting system that is distinct from the weighting system used for the primary air concentration value, and may be compared to a secondary threshold value that is different from the primary threshold value.

FIG. 5a depicts a primary weighting value curve 66a corresponding to a relatively large window volume $Qwindow_{primary}$. Note that the primary weighting value curve 66a gives reduced weighting to "older" values. Such a primary weighting value may be used to determine the primary air concentration value, which will be compared to a primary threshold value. FIG. 5b depicts a secondary weighting value curve 66b corresponding to a smaller window volume $Qwindow_{secondary}$, which may be used to determine a secondary air concentration value for comparison to a secondary threshold value. Note that smaller Qwindow values correspond to a shorter period during which the air values are given relevant weightings in determining air concentration values.

By having a larger Qwindow value, as shown in FIG. 5a, the primary air concentration value may represent the amount of air in the fluid introduced into the IV system over a relatively long period of time and/or fluid volume, depending on the flow rate. Such large Qwindow values are useful in detecting certain fluid flow anomalies where small amounts of air are introduced into the system over a long period, possibly building up to an unacceptable level. For example, conditions may develop in an IV system where a "train" of very small bubbles is introduced into the IV system over an extended period. Although the individual bubbles are very small and may not activate an alarm that looks at only a small period of time or volume, such a train of bubbles may, over a period of time or delivered fluid volume, introduce a significant amount of air into the system. By using a large Qwindow in combination with a relatively low threshold, the current invention can activate an alarm when such bubble trains occur.

The use of a large Qwindow with a relatively low threshold is helpful in detecting fluid flow anomalies that involve small amounts of air that are introduced into the IV system in a large volume of fluid and/or over a long period of time. However, a large Qwindow with a low threshold may not, by itself, always be the best method for detecting fluid flow anomalies. For example, where a large amount of air is introduced into the system over a very small fluid volume and/or a short period of time, but with little or no air previously introduced into the system, an air concentration value calculated with a large Qwindow may not exceed even a small threshold due to the weighting value. However, an air concentration value calculated under the same circumstances, but using a smaller Qwindow, will typically exceed an even larger threshold. The use of a small Qwindow with a relatively high threshold is thus helpful in rapidly detecting fluid flow anomalies that involve large amounts of air introduced into the system over a very small fluid volume and/or a short period of time.

The use of a primary air concentration with a large Qwindow and low threshold, in combination with a secondary air concentration value with a small Qwindow and a high threshold, allows the system to rapidly and efficiently detect long-term anomalies (e.g., trains of small bubbles) as well as short-term anomalies (e.g., large air bubbles introduced suddenly into the system). To increase a system's effectiveness in rapidly detecting medium-term anomalies (such as where a moderate amount of air is introduced into the system), a third air concentration value, with a medium-size Qwindow and a medium-size threshold, may be used. Depending on the specific IV system and the desired sensitivity, additional air concentration values may be included (i.e., fourth, fifth, etc. air concentration values), having differing thresholds and Qwindows. Note that the various air concentration calculations and threshold comparisons can be performed in parallel or tandem with each other.

Figure 5C:
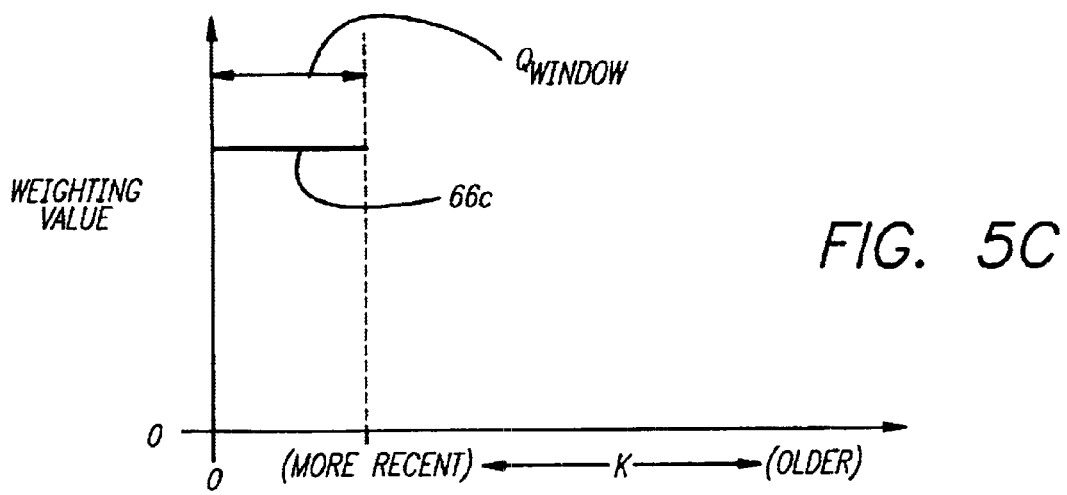
FIG. 5c is a graph depicting a constant weighting value as applied to various air signals.

As discussed above, the secondary air concentration value may be determined with a small Qwindow and a relatively high threshold to detect large amounts of air introduced into the system in a short period of time or in a small volume of fluid. Where Qwindow becomes very small, the weighting value plays less of a role in determining the air concentration value. For detecting large single bubbles that enter the IV system, such as may occur when the fluid supply reservoir becomes empty, the use of a varying weighting value may not be the most efficient approach, depending on the characteristics of the particular system. FIG. 5c depicts a constant weighting value 66c that can be applied to a select set of air values over a small Qwindow.

Figure 6:
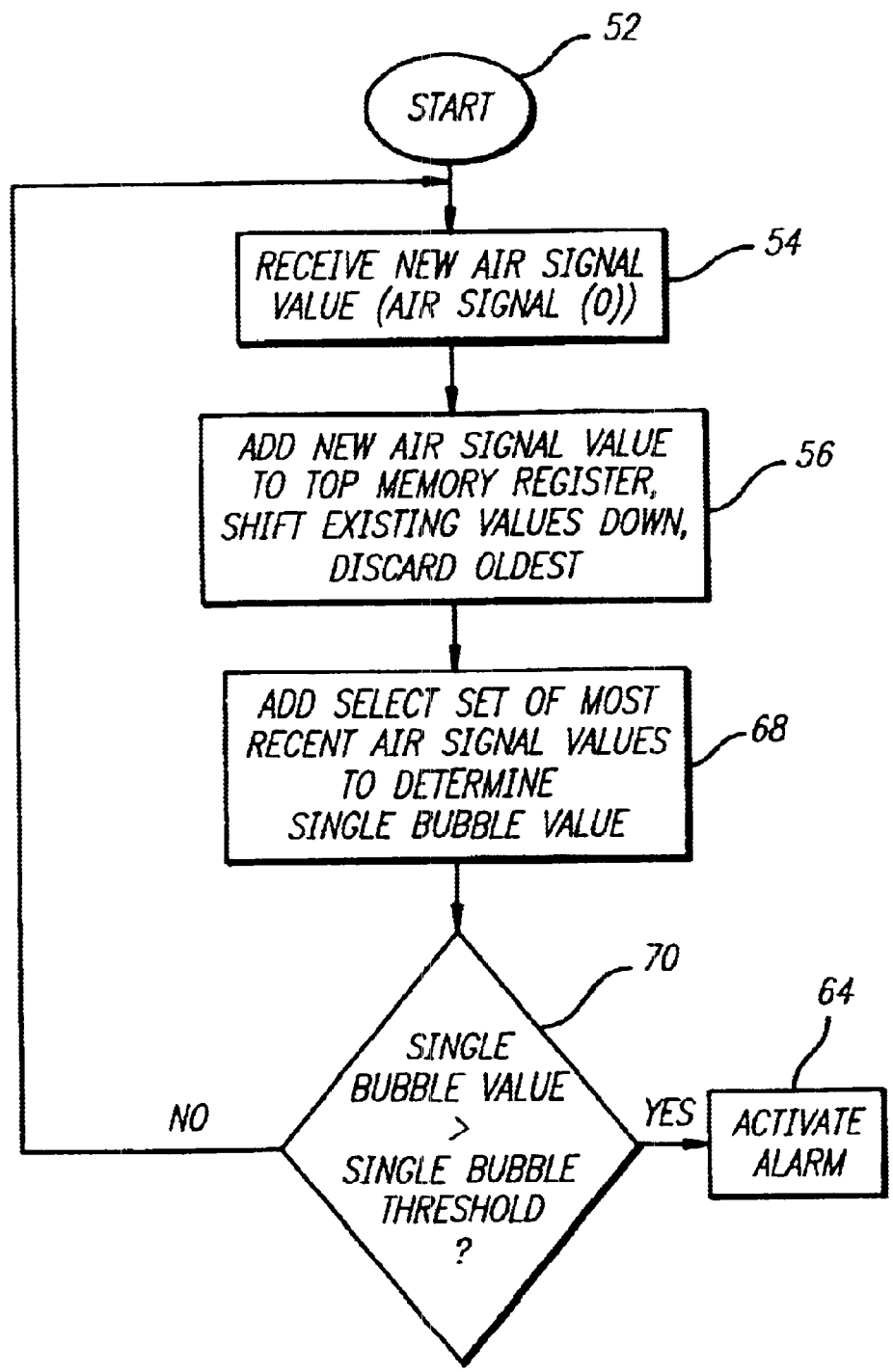
FIG. 6 is a simplified flowchart showing a process for determining air concentration in a fluid line according to a further embodiment of the invention.

In one embodiment of the invention, the secondary air concentration value is determined with a constant weighting value (as depicted in FIG. 5c), and the secondary air concentration value is compared to a single bubble threshold to detect large single bubbles. As shown in FIG. 6, after the newest air signal value has been added to the register at step 56, the processor takes a limited number of the most recent air signal values to determine the secondary air concentration value, also known as a single bubble value. The most recent air signal values would typically be a subset of the air signal values used to determine the primary air concentration value. In the embodiment of FIG. 6, the single bubble value is determined (at step 68) by merely adding the most recent air signal values, without the use of any weighting values. At step 70, the single bubble value is compared to the single bubble threshold. If the threshold is exceeded, then the alarm is sounded (step 64). Otherwise, the system repeats the cycle as new air signal values are received.

Storing a large number of air signal values may require a relatively large amount of memory registers, which may be undesirable in some circumstances. Additionally, independently multiplying large numbers of air signal values by different weighting values can be processor intensive. In one embodiment of the invention, the system uses a weighted past air concentration value, thus reducing the requirements for multiplication operations and memory. In such an embodiment the current air concentration value is determined as a function of the current air signal AirSignal(0) and a weighted version of the most recently calculated air concentration value (i.e., a weighted past air concentration value).

In determining the current air concentration value by using a weighted past air concentration value, a formula such as the following might be used:

$$\text{FilterOut}(0) = b \times \text{AirSignal}(0) + a \times \text{FilterOut}(1) \quad (4)$$

where:
AirSignal(0)=the most recent air signal value;
FilterOut(0)=the current air concentration value that will be compared with the alarm threshold;
FilterOut(1)=the previously calculated air concentration value;
a=a weighting factor ("PastWeight"); and
b=a weighting factor ("CurrentWeight").
Note that the value (a×FilterOut(1)) is the weighted past air concentration value.

The effect of such a formula is that older air signals have a lesser impact on the current air concentration value FilterOut(0). That is, the older air signal values are effectively given a lesser weighting. For example, using the above-cited formula, the most recent air signal value AirSignal(0) is given a fraction of its entire value by multiplying it by the weighting factor CurrentWeight (b). AirSignal(1), which had been used to determine FilterOut (1), would be effectively given a weighting value equal to PastWeight×CurrentWeight. AirSignal(2), which had been used to determine FilterOut(2) and thus also was a factor in calculating FilterOut(1), would effectively be given a weighting value of (PastWeight)$^2$×CurrentWeight. AirSignal (3) would effectively be given a weighting value of (PastWeight)$^3$×CurrentWeight, etc.

In a preferred embodiment, the weighting factor Past-Weight (a) is less than 1, so that the older air signal values will be given progressively less weight as they age. The air concentration value FilterOut(0) is thus calculated as a function of all of the air signal values, so that the number of air signal values that are used to calculated FilterOut(0) is not limited by a set number of memory registers.

Figure 7:
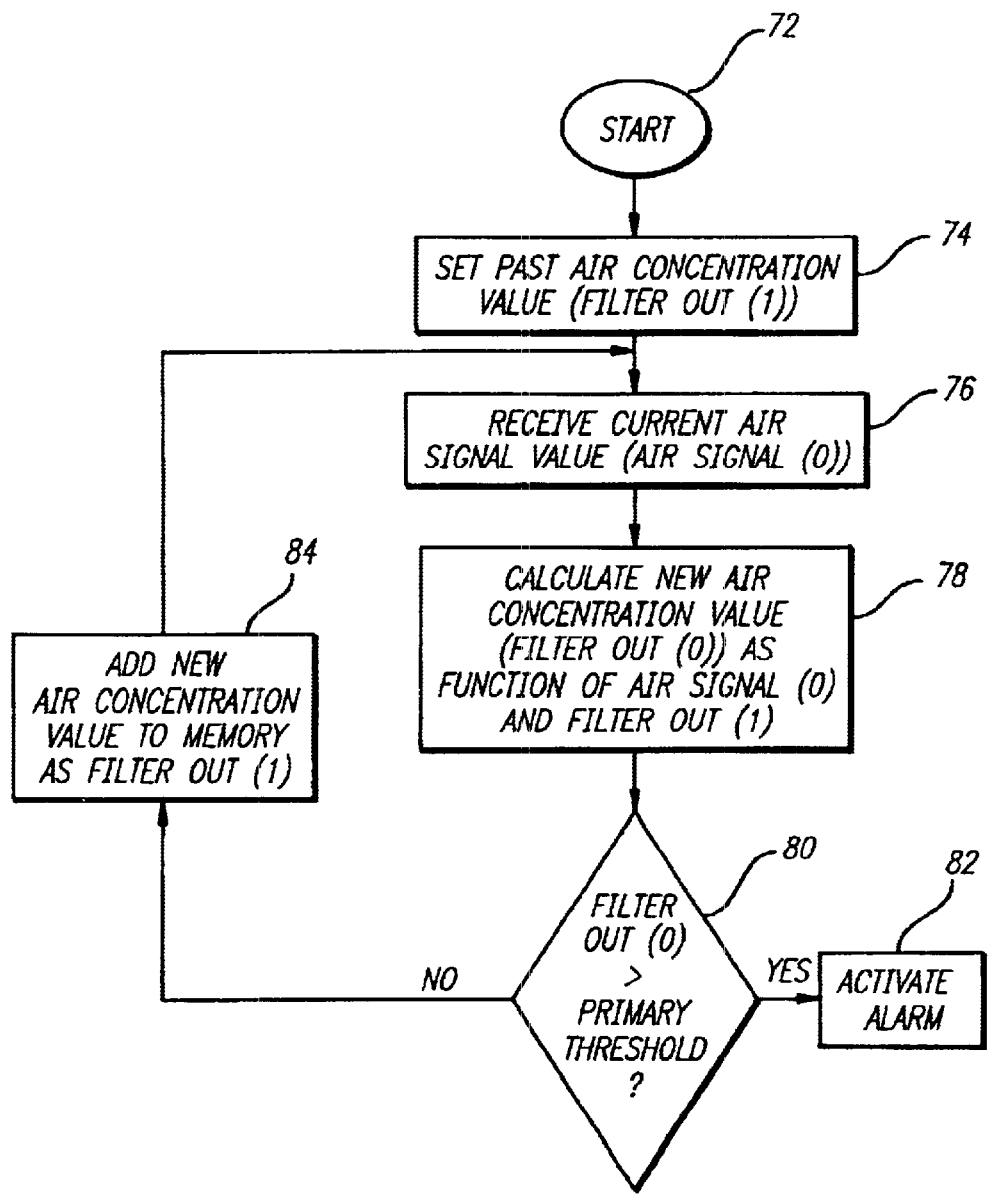
FIG. 7 is a simplified flowchart showing a process for determining air concentration in a fluid line according to a further embodiment of the invention.

FIG. 7 is a simplified flowchart depicting a process whereby the system uses a weighted past air concentration value instead of individually multiplying individual air signal values and weighting values. In the embodiment of FIG. 7, after initial start 72 (or manual reset) of the system, an initial FilterOut(1) value, which is below the alarm threshold, may be provided (at step 74) either as an initial input value or computed as a function of various factors, such as fluid volume, delivery rate, alarm threshold value, selected sensitivity, etc. As the system operates, a current air signal value AirSignal(0) is received (at step 76). At step 78, the processor determines a new air concentration value FilterOut(0), which is calculated as a function of AirSignal (0) and FilterOut(1). At step 80, the new air concentration value FilterOut(0) is compared to the primary threshold. If the primary threshold is exceeded, an alarm sounds (at step 82). If the new air concentration value is within the threshold limit, the current FilterOut(0) value becomes FilterOut(1) (at step 84), and the cycle repeats with receipt of a new air signal value (step 76).

Note that FIG. 7 is a simplified depiction of one embodiment of the invention. There may be numerous additional steps involved, depending on the particular embodiment. For example, the primary threshold may be set, either as a directly input value from the user or as a calculated value determined from various parameters such as fluid flow rate, patient characteristics (weight, age, etc.), the type of fluid involved, etc. Moreover, the primary threshold may, as discussed previously, be used in conjunction with additional thresholds to which are compared additional air concentration values.

Figure 8:
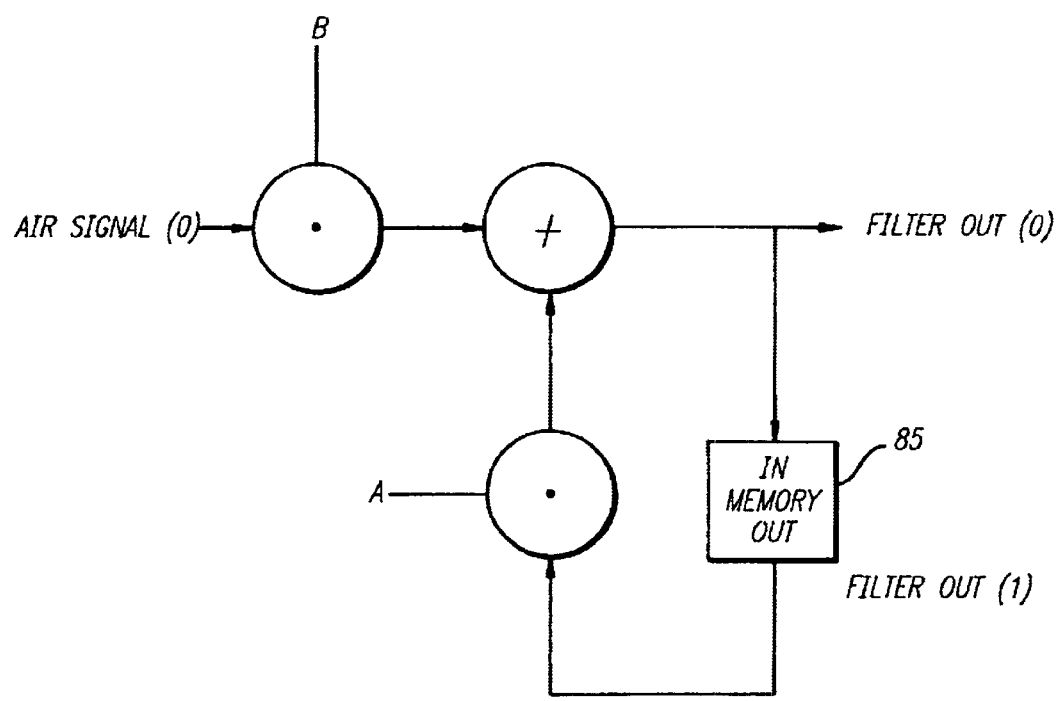
FIG. 8 is a signal flow diagram depicting the use of weighted past air concentration values.

The efficiency of the use of weighted past air concentration values, which is a recursive implementation referred to as an infinite impulse response (IIR) method, is shown in FIG. 8, which depicts a signal flow diagram for an embodiment of such a system. The values AirSignal(0), FilterOut (1), a, and b are used to derive each new FilterOut(0) value. Only one memory register 85 is required, which is used to store the previous filtered air concentration value FilterOut (1). Because the system is "recursive," i.e., uses past results to compute current results, it effectively applies weighting to all air signal values ever received, which in an IV system may be to the beginning of the infusion. For older air signals, however, the weighting will typically drop so close to zero as to be largely negligible.

In a further embodiment of the invention, the system uses a combination of direct weighting of recent air signal values along with a weighted past air concentration value. For example, as set forth in the following formula, the invention may apply a first weighting factor to the two most recent air signal values, which may be stored in memory registers, while a second weighting factor is applied to the most recently calculated air concentration value FilterOut(1):

$$FilterOut(0) = \left(\frac{Qsample}{Qsample + \frac{2 \times Qwindow}{3}}\right) \times (AirSignal(0) + AirSignal(1)) - \left(\frac{Qsample - \frac{2 \times Qwindow}{3}}{Qsample + \frac{2 \times Qwindow}{3}}\right) \times FilterOut(1) \quad (5)$$

where:
AirSignal(0)=the current air signal value;
AirSignal(1)=the next most recent air signal value;

FilterOut(0)=the current air concentration value that will be compared with the alarm threshold;

FilterOut(1)=the most recently calculated air concentration value;

Qsample=the volume of fluid moved in the sample; and

Qwindow=the size of the volume window.

In the particular embodiment shown in Equation 5, the weighting factor or multiplier for the current air signal value (AirSignal(0)) and immediately previous air signal value (AirSignal(1)) is a function of the volume of fluid moved in each sample (Qsample) and the size of the volume window (Qwindow). As the size of the volume window Qwindow is increased, the weighting factor generally decreases, thereby placing smaller weight on each individual air signal value. As the sample volume Qsample increases, the weighting generally increases to reflect the fact that the present air signal value is representing a larger volume increment.

The currently calculated air concentration value, FilterOut (0), in Equation 5 is thus determined using the immediate past air concentration value FilterOut(n), to which is applied a weighting term which is itself a function of Qwindow and Qsample. FilterOut(0) is also determined by applying a weighting factor directly to the two most recent air signal values AirSignal(0) and AirSignal(1).

Figure 9:
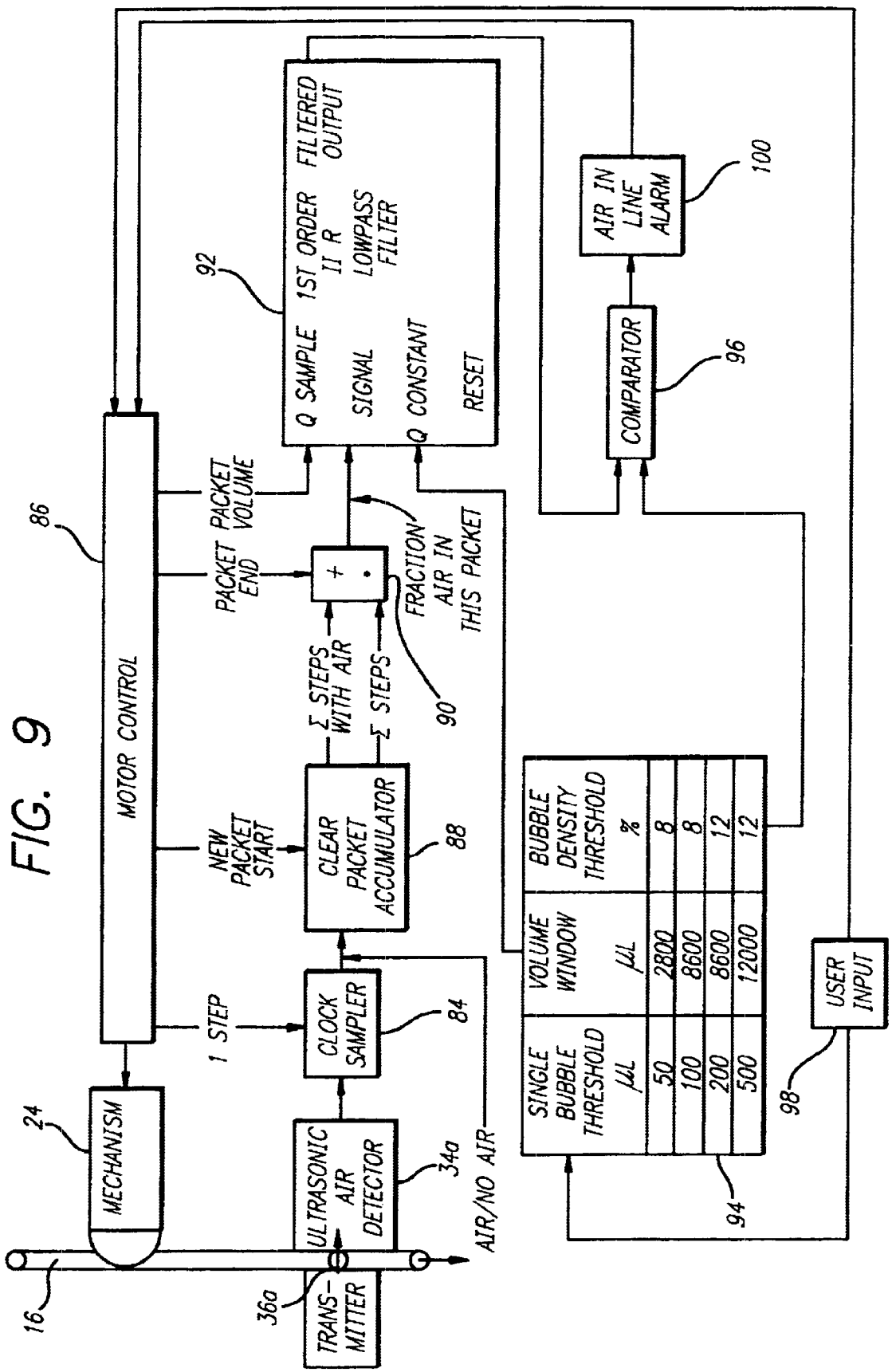
FIG. 9 is a simplified block diagram of a system for detecting air in a fluid line according to a further embodiment of the invention.

A particular embodiment of the invention is depicted in FIG. 9, in which a simple sensor 34a provides a binary signal indicating air or no air in the particular section 36a of the fluid conduit 16. The sensor 34a takes a sample each time that the pump mechanism 24 takes a step, so that the resulting binary air values represent either a step with air or a step without air. A clock sampler 84 provides values indicating to which pump motor step each binary air value corresponds.

With many peristaltic mechanisms driven by a step motor, the fluid flow varies widely from step to step, and some steps may even generate negative flow. Thus, the binary air values for various steps may have to be processed to account for the fluid that actually flowed during that step.

In the embodiment shown, the motor control 86 groups the steps in each pump cycle into several packets, so that each packet includes several pump steps. The fluid volume (Qsample) pumped in the particular packet may be of the same order of magnitude as the fluid volume pumped in the other packets. To achieve this result, the packets may have different numbers of step in them. The binary air values are provided to a packet accumulator 88 and sorted into values representing steps with air and values representing steps without air.

When the packet is completed, i.e., when the motor has stepped through all the steps in the packet, the number of steps with air are divided by the total number of steps, as shown at 90. The resulting value is an air fraction representing the amount of air introduced into the intravenous system during the pump steps of the packet. The air fraction is used, at 92, as an air signal value to determine the primary air concentration value. The system also uses a volume window size (Qwindow), which is shown provided by a memory 94, to calculate the primary air concentration value (FilterOut(0)), such as by using Equation 5 set forth above. The output primary air concentration value is compared, at 96, to a primary threshold provided by the memory 94. In the embodiment depicted, the primary threshold is a Bubble Density Threshold. The primary threshold may be selected by the user via an input device 98 such as a keyboard or similar control panel, which may also be used to input commands to the pump motor control 86 such as desired fluid flow rate, etc. The primary threshold may also be determined as a function of the selected flow rate, and/or as a function of the window volume Qwindow.

When the primary threshold is exceeded, an alarm 100 is activated. Alarm activation may also include shutting of the pump motor 24 through the pump motor control 86.

The memory 94 may also provide a secondary threshold value, which as depicted is a Single Bubble Threshold, to which is compared a secondary air concentration value. If the secondary threshold value is exceeded, the alarm 100 will a be activated.

Figure 10:
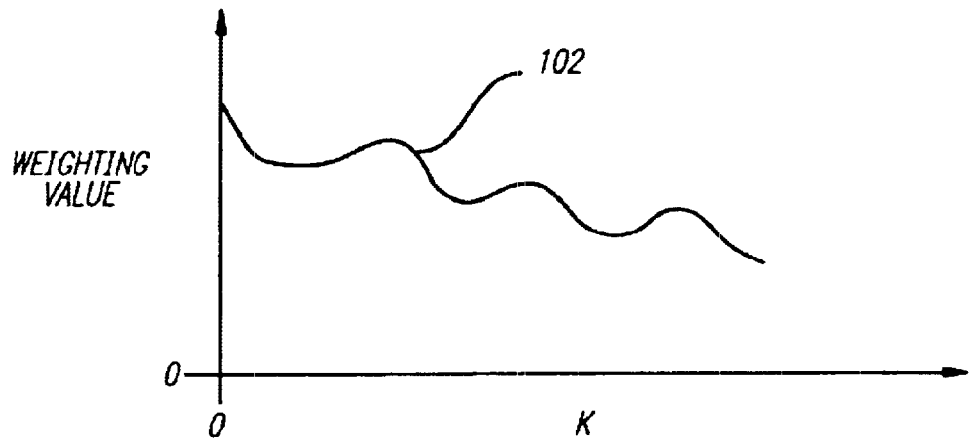
FIG. 10 is a graph depicting a varying weighting value curve as a function of the age of various air signals.

In the embodiments depicted in FIGS. 2 and 3, the weighting values are applied to the air signal values so as to cause older air signal values to be given decreasing weightings that follow a relatively smooth curve that gradually and exponentially tapers off. In other embodiments of the invention, however, weighting values may be used that follow non-exponential curves. For example, a simple linear decay may be used. Moreover, relatively complicated non-exponential curves can be created by varying the factors a and b. Thus, the "curve" of weighting values applied to air signal values as they age can be tailored as desired to suit varying circumstances. FIG. 10 depicts an example of such a non-exponential curve 102.

Figure 11:
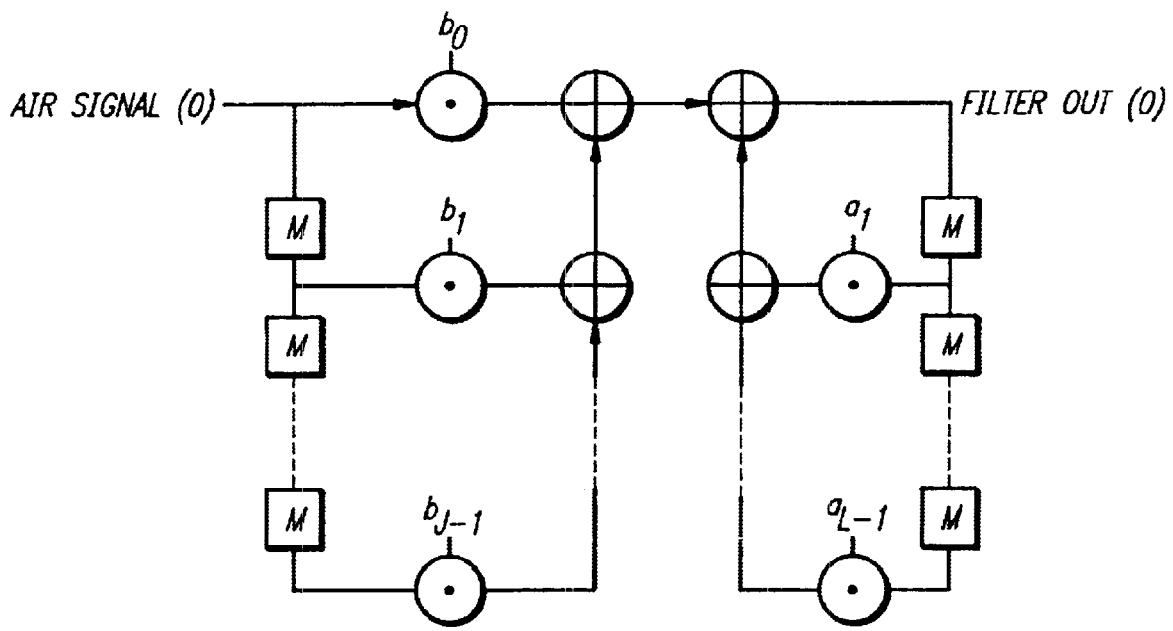
FIG. 11 is a signal flow diagram of an embodiment where the weighting factors a and b are varied.

FIG. 11 depicts a signal flow diagram wherein the values a and b are varied as the air signal values age. A "B" memory register having a number J of registers stores b values from $b_0$ to $b_{j-1}$. Similarly, an "A" memory register having a number L of registers stores a values from $a_1$ to $a_{L-1}$. AirSignal values from the current AirSignal(0) to the oldest AirSignal(L−1) are stored in an air signal memory having a number J−1 of registers. Similarly, previous air concentration values, from the most recent (AirConcentration(1)) to the oldest (AirConcentration(L−1)), are stored in an air concentration memory having a number L−1 of registers.

As a current air signal value AirSignal(0) is received, it is placed in the top (current) register in an air signal memory, which has J−1 registers, while previous air signal values, AirSignal(1) to AirSignal(L−1), are shifted down in the register. The weighting factor $b_0$ is applied to AirSignal(0), the factor $b_1$ is applied to AirSignal(1), etc., with the result used in the calculation of AirConcentration(0). The earlier values of AirConcentration are also used in determining the updated AirConcentration value. The weighting factor $a_1$ is applied to AirConcentration(1), the factor $a_2$ is applied to AirConcentration(2), etc. A desired formula for the final calculation of AirConcentration(0), such as a modified version of Equation 1 discussed above, may be selected to suit particular applications and circumstances. Thus, a final filtered output value of AirConcentration(0) can be a function of numerous past AirSignal values and AirConcentration values, to which have been applied many different weighting factors $a_1, a_2, \ldots, b_1, b_2, \ldots$.

Although preferred and alternative embodiments of the invention have been described and illustrated, the invention is susceptible to modifications and adaptations within the ability of those skilled in the art and without the exercise of inventive faculty. For example, while the examples above have generally been concerned with the use of light or sound to provide an instantaneous measurement of air in the line, other methods of determining instantaneous measurements of air in the line, such as pressure-sensitive devices, are also compatible with the invention. Moreover, numerous equations and formula may be used to determine air concentration values within the scope of the invention. In addition to detecting air, the invention may also be applied to the detection of other agents that might be introduced into a fluid delivery system. Thus, it should be understood that various changes in form, detail, and usage of the present invention may be made without departing from the spirit and scope of the invention. Accordingly, it is not intended that the invention be limited, except as by the appended claims.

What is claimed is:

1. An apparatus for detecting agents in a fluid delivery system in which fluid flows through a fluid conduit, the apparatus comprising:

an agent sensor adapted to be coupled to the fluid conduit for providing agent signals in response to agents sensed in the fluid conduit, said agent signals having an age; and a processor configured to receive the agent signals, determine weighted agent signals by applying weighting values to agent signals giving differing weighting to different agent signals depending on the age of each agent signal, and determine an agent concentration value from the weighted agent signals.

2. The apparatus of claim 1, wherein the processor further compares the agent concentration value to an alarm threshold and, in response to the agent concentration value exceeding the alarm threshold, provides an alarm signal, and wherein the apparatus further comprises:

an alarm that is activated by the alarm signal.

3. The apparatus of claim 1, further comprising:

a display for providing an indicia of the agent concentration value.

4. The apparatus of claim 1, further comprising:

a fluid control device, said fluid control device acting on a section of the fluid conduit to control the flow of fluid through the fluid conduit.

5. The apparatus of claim 4, wherein the processor controls the fluid control device.

6. The apparatus of claim 5, wherein the processor compares the agent concentration value to an alarm threshold and, in response to the agent concentration value exceeding the alarm threshold, causes the fluid control device to stop fluid from flowing through the fluid conduit.

7. The apparatus of claim 1, wherein the agent concentration value is determined by applying a weighting value to each agent signal as a separate calculation.

8. The apparatus of claim 1, wherein the processor is also configured to determine the agent concentration value by applying a weighting value to a past agent concentration value.

9. A fluid delivery system for introducing fluid to a patient from a fluid source, the system comprising:

a fluid conduit adapted to be downstream of and in fluid communication with the fluid source;

a cannula adapted to be in fluid communication and downstream of the fluid source and fluid conduit, the cannula configured to be introduced into a patient's body to provide fluid thereto;

a sensor coupled to the fluid conduit for providing agent signals in response to agents sensed in the fluid conduit, said agent signals each having an age; and a processor configured to receive the agent signals, determine weighted agent signals by applying a weighting value to each agent signal based on the age of the agent signal, and determine an agent concentration value by processing the weighted agent signals.

10. The system of claim 9, further comprising:

a fluid control device, said fluid control device acting on a section of the fluid conduit to control the flow of fluid through the fluid conduit.

11. The system of claim 10, wherein the processor controls the fluid control device.

12. The system of claim 11, wherein the processor compares the agent concentration value to an alarm threshold and, in response to the agent concentration value exceeding the alarm threshold, causes the fluid control device to stop fluid from flowing through the fluid conduit.

13. The system of claim 9, wherein the processor further compares the agent concentration value to an alarm threshold and, in response to the agent concentration value exceeding the alarm threshold, provides an alarm signal, and wherein the system further comprises:

an alarm that is activated by the alarm signal.

14. The system of claim 9, wherein the agent concentration value is determined by applying a weighting value to each agent signal as a separate calculation.

15. The system of claim 9, wherein the processor is also configured to determine the agent concentration value by applying a weighting value to a previous agent concentration value.

16. A method of detecting agents in a fluid delivery system in which fluid flows through a fluid conduit, the method comprising the steps of:

(a) providing a first series of agent signal values, wherein each agent signal value is indicative of the instantaneous amount of agent in a fluid conduit, and each agent signal has an age;

(b) determining one or more weighted agent signal values by applying a varying weighting value to one or more of the agent signal values based on the age of each agent signal value; and (c) determining a primary agent concentration value by processing the weighted agent signal values.

17. The method of claim 16, wherein step (b) includes the step of applying the varying weighting value to each agent signal as a separate calculation.

18. The method of claim 16, wherein step (b) includes the step of applying the weighting value to a past agent concentration value.

19. The method of claim 16, comprising the further steps of:

(d) comparing the primary agent concentration value to a first alarm threshold.

20. The method of claim 19, comprising the further step of:

(e) stopping the flow of fluid through the fluid conduit in response to the primary agent concentration value exceeding the first alarm threshold.

21. The method of claim 20, including the further steps of:

(f) providing a second series of agent signal values, wherein each agent signal value is indicative of the instantaneous amount of agent in a fluid conduit; and (g) processing the second series of agent signal values to determine a secondary agent concentration value.

22. The method of claim 21, wherein the second series of agent signal values is a subset of the first series of agent signal values.

23. The method of claim 21, comprising the further step of:

(h) comparing the secondary agent concentration value to a secondary alarm threshold.

24. An apparatus for detecting agents in a fluid delivery system in which fluid flows through a fluid conduit, the apparatus comprising:

an agent sensor adapted to be coupled to the fluid conduit for providing agent signals in response to agents sensed in the fluid conduit; and a processor configured to receive an agent signal, determine a weighted previous agent concentration value by applying a weighting value to a previous agent concentration value, and determine a current agent concentration value from the agent signal and the weighted previous agent concentration value.

25. The apparatus of claim 24, wherein the processor further compares the current agent concentration value to an alarm threshold and, in response to the current agent concentration value exceeding the alarm threshold, provides an alarm signal, and wherein the apparatus further comprises:

an alarm that is activated by the alarm signal.

26. The apparatus of claim 24, further comprising:

a display for providing an indicia of the current agent concentration value.

27. The apparatus of claim 24, further comprising:

a fluid control device, said fluid control device for acting on a section of the fluid conduit to control the flow of fluid through the fluid conduit.

28. A method of detecting agents in a fluid delivery system in which fluid flows through a fluid conduit, the method comprising the steps of:

(a) providing an agent signal value which is indicative of the instantaneous amount of agent in a fluid conduit;

(b) determining a weighted previous agent concentration value by applying a weighting factor to a previous agent concentration value;

(c) determining a primary agent concentration value by processing the agent signal value and the weighted previous agent concentration values.

* * * * *